(12) United States Patent
Reinhardt et al.

(10) Patent No.: US 9,816,647 B2
(45) Date of Patent: Nov. 14, 2017

(54) SEALING ELEMENT FOR A FLUIDIC CONNECTION

(75) Inventors: Thomas Reinhardt, Karlsruhe (DE); Joachim-Richard Wagner, Ettlingen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 432 days.

(21) Appl. No.: 14/403,503

(22) PCT Filed: May 22, 2012

(86) PCT No.: PCT/EP2012/059514
§ 371 (c)(1),
(2), (4) Date: May 5, 2015

(87) PCT Pub. No.: WO2013/174421
PCT Pub. Date: Nov. 28, 2013

(65) Prior Publication Data
US 2015/0233503 A1    Aug. 20, 2015

(51) Int. Cl.
*F16L 19/065* (2006.01)
*F16J 15/02* (2006.01)
(Continued)

(52) U.S. Cl.
CPC .......... *F16L 19/065* (2013.01); *F16J 15/022* (2013.01); *F16L 21/005* (2013.01); *G01N 30/60* (2013.01);
(Continued)

(58) Field of Classification Search
CPC ...... F16J 15/022; F16L 19/065; F16L 21/005; G01N 2030/027; G01N 30/60; Y10T 29/49826; Y10T 29/49872
See application file for complete search history.

(56) References Cited

U.S. PATENT DOCUMENTS 4,313,828 A    2/1982  Brownlee
4,451,364 A *  5/1984  Higgins ............... F16L 19/065
                                                210/198.2
(Continued)

FOREIGN PATENT DOCUMENTS

CN    102239408 A    11/2011
CN    102439437 A    5/2012
(Continued)

OTHER PUBLICATIONS

Office Action and Search Report dated Sep. 6, 2015 by the State Intellectual Property Office of the People's Republic of China with regard to the related Application No. 201280073391.9.
(Continued)

*Primary Examiner* — Francis Gray

(57) ABSTRACT

A sealing element for sealing a fluidic connection between a coupling element and a tubular element and thereby providing a sealed flow path through the tubular element and between the coupling element and the tubular element in a longitudinal direction, the sealing element comprising: a recess extending in the longitudinal direction, the recess configured to receive the tubular element; a transverse wall defining an extent of the recess in the longitudinal direction, the transverse wall having a through hole.

20 Claims, 4 Drawing Sheets

(51) Int. Cl.
*F16L 21/00* (2006.01)
*G01N 30/60* (2006.01)
*G01N 30/02* (2006.01)

(52) U.S. Cl.
CPC ... *G01N 2030/027* (2013.01); *Y10T 29/49826* (2015.01); *Y10T 29/49872* (2015.01)

(56) References Cited

U.S. PATENT DOCUMENTS

| | | | |
|---|---|---|---|
| 4,690,437 | A | 9/1987 | Anderson, Jr. |
| 4,982,597 | A | 1/1991 | Berger |
| 5,582,723 | A * | 12/1996 | Boone ............... G01N 30/6091 210/198.2 |
| 8,608,210 | B2 * | 12/2013 | Kainec ................ F16L 19/00 285/343 |
| 2011/0298210 | A1 | 12/2011 | Hochgraeber et al. |
| 2012/0061955 | A1 * | 3/2012 | Hochgraeber ..... G01N 30/6026 285/342 |
| 2012/0119491 | A1 | 5/2012 | Jevdokimov |

FOREIGN PATENT DOCUMENTS

| | | |
|---|---|---|
| DE | 102009022368 B3 | 11/2010 |
| WO | WO2005084337 A2 | 9/2005 |
| WO | 2012010222 A1 | 1/2012 |
| WO | WO2012010222 A1 | 1/2012 |
| WO | WO2012/116753 A1 | 9/2012 |

OTHER PUBLICATIONS

International Search Report dated May 22, 2012 for Application No. PCT/EP2012/059514.

* cited by examiner

SEALING ELEMENT FOR A FLUIDIC CONNECTION

The present application is a national stage application under 35 U.S.C. §371 and claims priority under 35 U.S.C. §121 from International Patent Application No. PCT/EP2012/059514 filed on May 22, 2012. The entire disclosure of International Patent Application No. PCT/EP2012/059514 is specifically incorporated herein by reference.

BACKGROUND ART

The present invention relates to a sealing element for a fluidic connection in a fluidic device, in particular in a high performance liquid chromatography application.

In high performance liquid chromatography (HPLC), a liquid has to be provided usually at a very controlled flow rate (e.g. in the range of μl to ml/min) and a high pressure (typically 20 to 100 MPa, 200 to 1.000 bar and beyond up to currently 200 MPa, 2.000 bar) at which compressibility of the liquid becomes noticeable.

For providing fluidic connections, tubular elements such as tubings are used. A typical tubular element used in a HPLC application is a glass capillary having an outer diameter of 1 millimeter or less.

Sealingly coupling a tubular element with a coupling element may be a complex task, in particular if the diameter of the tubular element is small or if the tubular element comprises a brittle material. Moreover, the sealed connection of the tubular element with the coupling element should have little or no dead volume and should not undergo "breathing", where fluid enters/exits free spaces in the connection if the pressure changes.

WO 2005/084337 relates to connectors for tube assemblies and in particular to a self-setting high pressure fitting for creating a high pressure seal. The coupling element comprises a male sealing element having a first end, a second end and a longitudinal access extending between the first end and the second end, wherein the male sealing element has a generally cylindrical shape and wherein the first end defines a conical sealing surface, wherein the conical sealing surface has a mismatch angle to a female sealing element and wherein the female sealing element defines a complementary conical geometry.

U.S. Pat. No. 4,690,437 discloses a low pressure fitting wherein a ferrule has a cylindrical forward portion which is substantially wider than the diameter of a tubing. An end surface of this forward portion is configured to mate with and sealingly engage an end wall surrounding a port of a fluid conducting member. The ferrule is constructed of a resilient deformable plastic material.

Usually at least one of a handling of a sealing element or the manufacture of the sealing element requires complex actions.

DISCLOSURE

It is an object of the herein disclosed subject matter to provide an improved fitting, in particular for HPLC applications.

According to an exemplary embodiment of a first aspect of the herein disclosed subject matter, a sealing element for sealing a fluidic connection between a coupling element and a tubular element is provided, the sealing element thereby providing a sealed flow path through the tubular element and between the coupling element and the tubular element in a longitudinal direction, the sealing element comprising: a recess extending in the longitudinal direction, the recess being adapted for receiving the tubular element; a transverse wall defining an extend of the recess in the longitudinal direction, the wall having a through hole.

The through hole in the wall provides for the flow part between the coupling element and the tubular element in the longitudinal direction. According to an embodiment, the coupling element is configured for receiving the sealing element and the tubular element, wherein the tubular element is located in the recess of the sealing element to thereby provide the sealed flow path between the coupling element and the tubular element. Embodiments of the herein disclosed subject matter allow a sealed fluidic connection between the coupling element and the tubular element, wherein the fluidic connection is configured for withstanding a pressure of at least 200 bar, optionally a pressure of at least 500 bar, or, in another embodiment the fluidic connection is configured to withstand a pressure of at least 1.000 bar, 2000 bar or more.

Embodiments of the herein disclosed subject matter allow the sealing of a fluidic connection between the coupling element and the tubular element which meets the requirements of a chromatography application, for example a liquid chromatography application such as a HPLC application. Chromatography applications require a low dead volume in the flow path of a mobile phase in order to increase accuracy of the chromatography and to avoid carry-over of a sample of a first measurement to a second measurement as far as possible.

It is to be understood that in particular the front faces in the connection of the tubular element to the coupling element are often very difficult to seal as in particular the shape of the counterpart element of the coupling element to the tubular element might vary from one fluidic device to another and/or might have surfaced imperfections. Moreover, contact pressure in particular in the longitudinal direction may be limited in order to avoid or reduce destruction or deformation of the components involved, for example of the tubular element. In particular if the tubular element comprises or consists of glass, the contact pressure may be limited. With increasing fluid pressure, for example in the range of 1.000 bar and beyond, conventional sealing elements have been often shown to be not sufficient and may lead to leaking and/or cross contamination. A sealing element in accordance with embodiments of the herein disclosed subject matter may be capable of sealing a high pressure fluidic connection and may meet the needs of a chromatography application in regard of dead volume and/or cross contamination.

According to an embodiment, the recess comprises at least one retaining element for retaining the tubular element in the recess. The retaining element may ease handling of the sealing element since it allows mounting of the sealing element to the tubular element without danger that the sealing element falls off the tubular element before both are mounted to the coupling element. In accordance with an embodiment, the tubular element is plugged into the recess of the sealing element and is retained in the plugged-in position by the retaining element. This facilitates positioning of the assembly sealing element plus tubular element with respect to the coupling element.

According to a further embodiment, the sealing element includes at least three of the retaining elements. Three or more retaining elements may unambiguously define the position of the tubular element in the sealing element. According to an embodiment, the at least three retaining elements are spaced from each other in a circumferential direction. For example, according to an embodiment the retaining elements are provided in the sealing element so as to be positioned around the tubular element when the tubular element is located in the recess of the sealing element.

According to an embodiment, the retaining element is configured for exerting a radially inwardly directed force onto the tubular element. For example, according to an embodiment the retaining element retains the tubular element in the sealing element by friction. Hence, the retaining force that has to be overcome to remove the tubular element from the sealing element is defined by the radially inwardly directed force of the retaining element onto the tubular element.

According to a further embodiment, the retaining element is a protrusion located in the recess of the sealing element. According to a further embodiment, the retaining element is formed in the recess by a straight wall portion extending between two curved wall portions flanking the straight wall portion in circumferential direction. For example, the recess in the sealing element may be generally of a curved shape, for example of a circular shape, formed by curved wall wherein the protrusions protrude from this curved wall into the recess. According to another embodiment, the retaining element is formed as increased wall thickness extending radially inwardly, in particular extending radially inwardly as much as necessary to clamp and/or center the tubular element wherein optionally at least three retaining elements are present.

According to an embodiment, the circumferential direction referred to herein is a circumferential direction perpendicular to the longitudinal direction defined by the recess extending in the longitudinal direction and/or by the longitudinal direction defined by the tubular element.

According to an embodiment, the sealing element comprises a conical outer surface portion, the conical outer service portion having a diameter increasing in a direction from the transverse wall towards the recess. Hence, according to an embodiment the diameter of the sealing element increases in a direction from the transverse wall towards the recess. According to an embodiment, the sealing element comprises an inner surface portion defining the recess, wherein the inner surface portion is opposite the conical outer surface portion. Hence, in an embodiment the conical outer surface portion may be in a longitudinal range over which the recess of the sealing element extends.

According to an embodiment, the direction from the transverse wall towards the recess is a direction from the transverse wall through the recess and out of the recess. According to a further embodiment, the direction from the transverse wall towards the recess is the direction along which the tubular element extends when being located in the recess of the sealing element.

According to an embodiment, the inner surface portion and the conical outer surface portion diverge from each other in the direction from the transverse wall towards the recess. For example, in an embodiment the thickness of a wall of the sealing element increases in the direction from the transverse wall towards the recess, wherein the longitudinal wall provides the conical outer surface portion as well as the inner surface portion which defines the recess of the sealing element.

According to an embodiment, the inner surface portion and the conical outer surface portion are formed by a first longitudinal wall portion with a radial thickness that increases in the direction from the transverse wall towards the recess.

According to an embodiment, the sealing element comprises a cylindrical outer surface portion having a constant diameter in the longitudinal direction. For example, according to an embodiment, the cylindrical outer surface portion may be located in a longitudinal range of the sealing element where at least one retaining element is provided.

According to a further embodiment, the cylindrical outer surface portion is the outer surface of a second longitudinal wall portion. According to an embodiment, the second longitudinal wall portion is located between the transverse wall and the conical outer surface portion. For example, according to an embodiment the second longitudinal wall portion is located between the transverse wall and the first longitudinal wall portion.

According to an embodiment, the second longitudinal wall portion has a radial wall thickness that is constant in the direction from the transverse wall towards the recess.

According to an embodiment, the sealing element comprises a compression surface being spaced from the transverse wall. For example, according to an embodiment the compression surface is the outer surface of a third longitudinal wall portion of the sealing element. According to an embodiment, the third longitudinal wall portion comprises a cutout extending in the longitudinal direction. Optionally the longitudinal slit has a sharp-edged end in direction to the sealing face. According to a further embodiment, the longitudinal slit optionally has a rectangular end or a rounded end. According to a further embodiment, the third longitudinal wall portion comprises two cutouts. According to a further embodiment, the third longitudinal wall portion comprises three or more cutouts and wherein optionally the three or more cutouts are evenly spread or nonuniformly distributed over the circumference. Optionally, one or more cutouts in the third longitudinal wall portion, e.g. each cutout in the third longitudinal wall portion, is longitudinal slit.

According to an embodiment, the compression surface has a conical shape with a diameter decreasing in the direction from the transverse wall to the tubular element. According to an embodiment, the transverse wall forms a first end of the sealing element and the compression surface forms a second end of the sealing element, the second element being opposite the first end. According to an embodiment, the compression surface is spaced from the second end of the sealing element. According to an embodiment, the second end is opposite the first end in the longitudinal direction. According to a further embodiment, the compression surface faces the second end of the sealing element.

The compression surface may be used to push the sealing element in a direction towards the coupling element. For example, according to an embodiment, the compression surface may be used to push the sealing element towards the coupling element in the longitudinal direction.

According to an embodiment, the sealing element comprises at least one of the following features: the sealing element comprises a polymer; the sealing element comprises a polyether; the sealing element comprises polyetheretherketone; the sealing element consists of a polymer; the sealing element consists of a polyether; the sealing element consists of polyetheretherketone.

According to an embodiment, the sealing element is formed as a single piece. For example, according to a further embodiment the sealing element is a molded single piece. According to an embodiment, the sealing element is injection molded as a single piece.

According to an embodiment of a second aspect of the herein disclosed subject matter, a connection assembly is provided, the connection assembly comprising a coupling element; a tubular element fluidically connectable or fluidically connected to the coupling element; and a sealing element according to one or more embodiments of the herein disclosed subject matter; the connection assembly providing a connected state in which the tubular element is fluidically connected to the coupling element.

According to an embodiment, the coupling element has a recess for receiving the sealing element. According to a further embodiment, in the connected state the recess of the coupling element is arranged coaxially with the recess of the sealing element. However, this is not necessarily required and according to other embodiments the recess of the coupling element is not coaxially arranged with the recess of the sealing element.

According to an embodiment, the coupling element comprises a through hole, wherein the connected state the through hole of the coupling element is fluidically coupled to the through hole of the transverse wall of the sealing element. Hence, according to an embodiment a sealed flow path is provided through the tubular element, through the through hole in the transverse wall and through the through hole of the coupling element.

According to an embodiment, the diameter of the through hole of the coupling element is larger than the diameter of the through hole of the transverse wall of the sealing element. According to a further embodiment, the diameter of the through hole of the transverse wall of the sealing element is smaller than the inner diameter of the tubular element. Hence, in an embodiment, the diameter of the through hole in the transverse wall of the sealing element is the smallest diameter of the flow path in the vicinity of the sealing element. This may increase the sealing capability and may in particular increase the pressure resistance of the sealing.

According to an embodiment, the sealing element comprises the conical outer surface portion having a diameter increasing in a direction from the transverse wall towards the recess of the sealing element and the recess of the coupling element comprises a conical inner surface portion having a diameter which increases in a direction pointing outwardly from the recess of the coupling element through an opening which is defined by the recess of the coupling element and through which the sealing element is inserted; and wherein in the connected state the conical inner surface portion of the coupling element and the conical outer surface portion of the sealing element at least partially overlap in longitudinal direction. According to an embodiment, in the connected state the conical outer surface portion of the sealing element contacts the conical inner surface portion of the coupling element. The contact area in which a contact between the conical outer surface portion of the sealing element and the conical inner surface portion of the coupling element occurs may vary depending on a pressure with which the sealing element is pushed into the recess of the coupling element.

According to an embodiment, the conical inner surface portion of the coupling element has a first slope and the conical outer surface portion of the sealing element has a second slope. In an embodiment, the first slope is identical to the second slope. According to another embodiment, the first slope and the second slope are different. The different slope may provide for an increased movability of the sealing element with regard to the coupling element in longitudinal direction while still providing a contact between the conical outer surface portion of the sealing element and the conical inner surface portion of the coupling element. According to an embodiment, the second slope is steeper with regard to the longitudinal direction than the first slope. According to another embodiment, the first slope is steeper with regard to the longitudinal direction than the second slope. This may have the advantage that even under a slight movement of the sealing element in a direction out of the recess of the coupling element the contact area between the conical outer surface portion of the sealing element and the conical inner surface portion of the coupling element is only slightly reduced. Moreover, in such an embodiment, an inner boundary of the contact area, which faces a bottom of the recess of the coupling element, may stay in place even if the sealing element slightly moves with regard to the coupling element. Hence, breathing of the seal provided by the sealing element may be avoided or at least reduced. Further, such a configuration may be advantageous if the connection assembly is operated under high pressure such as the pressure is disclosed herein, which may range in exemplary embodiments from 200 bar to 1.000 bar and beyond.

According to an embodiment, the coupling element and the sealing element are configured such that without axial pressure on the sealing element only a contact portion of the conical outer surface of the sealing element contacts the conical inner surface of the coupling element, wherein the contact portion has a smaller area than the conical outer surface portion. According to an embodiment, the coupling element and the sealing element are configured such that a contact portion of the sealing element is facing the transverse wall of the sealing element (hence, the contact portion faces the bottom of the recess of the coupling element).

According to an embodiment, the sealing element is configured to have a cylindrical outer surface portion having a constant diameter in the longitudinal direction; and the recess of the coupling element comprises a cylindrical inner surface portion, wherein the connected state the cylindrical inner surface portion of the coupling element and the cylindrical outer surface portion of the sealing element at least partially overlap in longitudinal direction. According to an embodiment, in the connected state the cylindrical inner surface portion of the coupling element and the cylindrical outer surface portion of the sealing element are radially spaced from each other, at least if no pressure is exerted on the sealing element in the longitudinal direction, e.g. into the recess of the coupling element. This may allow for an easier insertion of the sealing element into the recess of the coupling element. Further, if retaining elements of the sealing element are provided in the recess of the sealing element in a longitudinal range of the sealing element over which the cylindrical outer surface portion of the sealing element extends, a slight increase of the outer diameter of the cylindrical outer surface portion of the sealing element due to insertion of the tubular element into the sealing element does not prevent the sealing element and the tubular element from being inserted into the recess of the coupling element.

According to a further embodiment, the sealing element is configured such that in the connected state the second longitudinal wall portion, which forms the cylindrical outer surface portion of the sealing element, is compressed in the longitudinal direction so as to expand in radial direction and thereby reduce a space between the cylindrical inner surface portion of the coupling element and the cylindrical outer surface portion of the sealing element. According to an embodiment, compression of the second longitudinal wall portion of the sealing element in longitudinal direction is such that the cylindrical outer surface portion of the sealing element contacts the cylindrical inner surface portion of the coupling element.

According to an embodiment, the sealing element comprises the compression surface being spaced from the transverse wall according to embodiments of the herein disclosed subject matter; and the connection assembly further comprises a pressing element for pressing against the compression surface. Hence, by action of the pressing element a pressing force is exerted onto the compression surface of the sealing element, pushing the sealing element into the recess of the coupling element.

According to an embodiment, the pressing element has a pressing surface. According to an embodiment, the pressing element is configured for pressing the sealing element into the recess of the coupling element. According to an embodiment, a compression of the sealing element by movement of the pressing element includes the transverse wall of the sealing element contacting the recess of the coupling element. Further, according to an embodiment compression of the sealing element by movement of the pressing element includes the conical outer surface portion of the sealing element at least partially contacting the conical inner surface portion of the coupling element. According to a further embodiment, compression of the sealing element by movement of the pressing element includes compressing the second longitudinal wall portion of the sealing element in the longitudinal direction. According to a further embodiment, compression of the sealing element by movement of the pressing element results in the sealing element radially pressing against the tubular element located in the recess of the sealing element. According to an embodiment, this results in a frictional engagement of the tubular element and the sealing element. For example, if the third longitudinal wall portion of the sealing element comprises a cutout, exertion of a pressure on the compression surface by the pressing element may reduce the size of the cutout by movement of the opposing portions of the third longitudinal wall portion towards each other in radial direction and hence towards the tubular element located in the recess of the sealing element. For example, in order to assist pressing of the sealing element on the tubular element located in the recess of the sealing element, the pressing surface may have a conical shape with an increasing diameter in a direction from the pressing element towards the transverse wall of the sealing element.

According to a further embodiment, the tubular element has a first hardness and the sealing element has a second hardness that is larger than the first hardness. As the hardness of a material is indicative of the plastic deformation of the material under pressure, this means that the sealing element is subject to more plastic deformation than the tubular element which may facilitate or even provide for implementation of embodiments of the herein disclosed subject matter.

According to an embodiment, the tubular element comprises silicon dioxide. According to a further embodiment, the tubular element comprises a glass. According to a further embodiment, the tubular element comprises fused silica. According to a further embodiment, the tubular element comprises steel. According to a further embodiment, the tubular element comprises a body and a layer covering the body. For example, according to an embodiment, the layer covering the body of the tubular element is a protective layer. For example, according to an embodiment, the body of the tubular element is made of fused silica and the layer covering the body is made of a polymer such as polyetheretherketon. According to a further embodiment, the layer covering the body comprises two or more sub-layers.

According to an embodiment, the coupling element is a fitting. According to a further embodiment, the tubular element is a capillary. According to a further embodiment, the coupling element and the tubular element are parts of a measuring device, such as a measuring device for performing a measurement on a fluidic sample, for example a liquid chromatography device or, more particularly a HPLC device.

According to a further embodiment, the sealing element is configured for providing a sealed fluidic connection between the coupling element and the tubular element, wherein the fluidic connection in configured to withstand a pressure of at least 200 bar, optionally a pressure of at least 500 bar, further optionally a pressure of at least 1.000 bar, further optionally a pressure of at least 1.500 bar, further optionally a pressure of at least 2.000 bar, or beyond.

According to an embodiment of a third aspect of the herein disclosed subject matter a measuring device for performing a measurement on a fluidic sample is provided, the measurement device comprising a fluidic device; and a connection assembly according to one or more embodiments of the herein disclosed subject matter, e.g. for coupling the tubular element for conducting the fluidic sample to the fluidic device.

Embodiments of the herein disclosed subject matter may be advantageous for use in a measuring device adapted for performing a measurement on a fluidic sample. However, according to other embodiments, the sealing element according to one or more embodiments of the herein disclosed subject matter or a connection assembly according to one or more embodiments of the herein disclosed subject matter may be employed in any suitable device which requires a sealed fluidic connection between a coupling element and a tubular element.

According to an embodiment, the fluidic sample is a mobile phase and the measuring device is a fluid separation system for separating compounds of a sample fluid in the mobile phase. According to a further embodiment, the fluid separation system comprises a mobile phase drive, preferably a pumping system, configured to drive the mobile phase through the fluid separation system. According to a further embodiment, the fluidic device is a separation unit, preferably a chromatographic column, configured for separating compounds of the sample fluid in the mobile phase.

According to an embodiment of a fourth aspect, a method for providing a fluidic connection between a coupling element and a tubular element is provided, the method comprising providing a connection assembly according to one or more embodiments of the herein disclosed subject matter; inserting the tubular element into the sealing element; inserting the sealing element into the recess of the coupling element.

According to an embodiment, the sealing element comprises the compression surface spaced from the transverse wall and the connection assembly comprising a pressing element for pressing against the compression surface, wherein the method further comprises operating the pressing element so as to press the sealing element into the recess of the coupling element. According to a further embodiment, the method comprises at least one of the following features: operating the pressing element so as to press the sealing element into the recess of the coupling element; wherein optionally the method further comprises at least one of the following features: pressing the transverse wall of the sealing element in contact with the recess of the coupling element; pressing at least part of the conical outer surface portion of the sealing element into contact with the conical inner surface portion of the coupling element; longitudinally compressing the sealing element so as to longitudinally compress the second longitudinal wall portion of the sealing element in longitudinal direction; compressing the sealing element so as to radially press the sealing element against the tubular element located in the recess of the sealing element; frictionally engaging the tubular element by the sealing element and moving together the sealing element and the tubular element deeper into the recess so as to compress the transverse wall between the tubular element and a bottom of the recess of the coupling element opposite the transverse wall.

The mobile phase (or eluant) can be either a pure solvent or a mixture of different solvents. It can be chosen e.g. to minimize the retention of the compounds of interest and/or the amount of mobile phase to run the chromatography. The mobile phase can also be chosen so that the different compounds can be separated effectively. The mobile phase might comprise an organic solvent like e.g. methanol or acetonitrile, often diluted with water. For gradient operation water and organic are delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid may be a liquid but may also be or comprise a gas and/or a supercritical fluid (as e.g. used in supercritical fluid chromatography—SFC—as disclosed e.g. in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

According to an embodiment, the tubular element is a tubing. The terms "radial" and "longitudinal", as used herein, shall, accordance to an embodiment, be defined with respect to the tubular element (e.g. the tubing) having an longitudinal direction in the direction of the fluid flow and a radial direction perpendicular to the longitudinal direction. The tubular element extends in longitudinal direction, and the flow path of the tubular element is circumferentially enclosed by the tubular element.

The terms "fitting" and "fitting element", as used herein, shall both relate to coupling a tubular element to a fluidic device. The term "fitting" shall cover all components required for coupling the tubular element to the fluidic device, and may even comprise the tubular element and/or the fluidic device, or parts thereof.

Embodiments of the present invention might be embodied based on most conventionally available HPLC systems, such as an Agilent 1200 Infinity Series LC System, or the Agilent 1100 HPLC series (all provided by the applicant Agilent Technologies—see www.agilent.com—which shall be incorporated herein by reference).

The fluid separation system may comprise a chromatographic column providing the stationary phase. The column might be a glass, plastic material, ceramic or steel tube (e.g. with a diameter from 50 micrometer to 5 millimeter and a length of 1 centimeter to 1 meter) or a microfluidic column (as disclosed e.g. in EP 1577012 or the Agilent 1200 Infinity Series.

In the above there has been described and in the following there will be described exemplary embodiments of the subject matter disclosed herein with reference to a sealing element, to a connection assembly, to a measuring device and to a respective method. It has to be pointed out that of course any combination of features relating to different aspects of the herein disclosed subject matter is also possible. In particular, some embodiments have been or will be described with reference to apparatus type features whereas other embodiments have been or will be described with reference to method type features. However, a person skilled in the art will gather from the above and the following description that, unless otherwise notified, in addition to any combination of features belonging to one aspect also any combination between features relating to different aspects or embodiments, for example even between features of the apparatus type embodiments and features of the method type embodiments is considered to be disclosed with this application.

According to embodiments of the herein disclosed subject matter, apparatus type features are adapted for providing the functionality of one or more of the embodiments of the method type features and/or for providing the functionality as required by one or more of the method type features.

According to further embodiments of the herein disclosed subject matter, method type features are adapted for providing the functionality of one or more of the embodiments of the apparatus type features and/or for providing the functionality as required by one or more of the apparatus type features.

The aspects and embodiments defined above and further aspects and embodiments of the present invention are apparent from the examples to be described herein after and are explained with reference to the drawings but to which the invention is not limited.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs. The illustration in the drawings is schematic.

Figure 1:
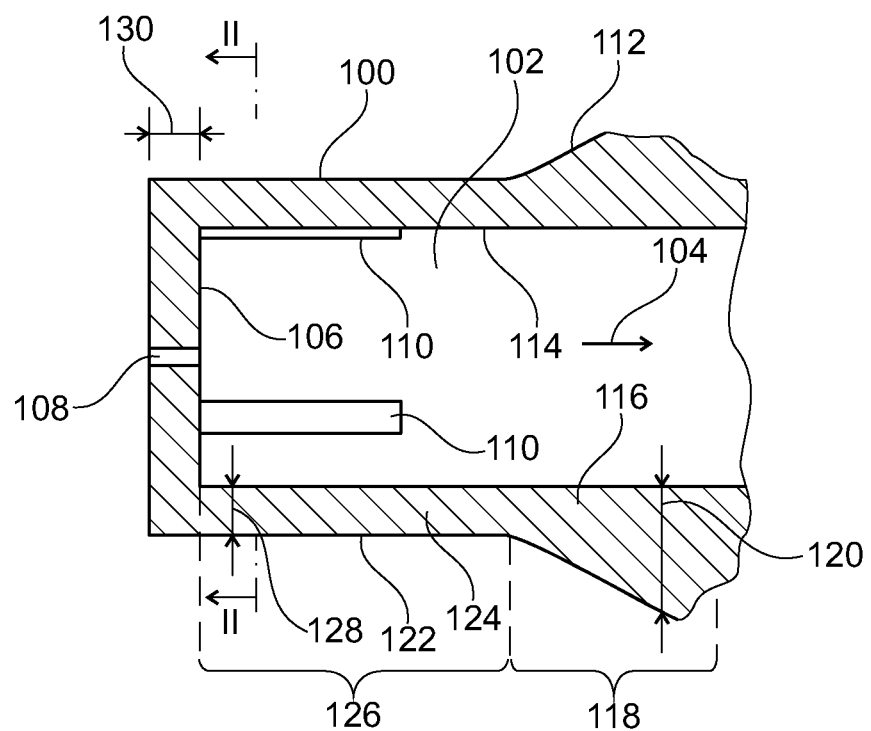
FIG. 1 illustrates a sealing element according to embodiments of the herein disclosed subject matter.

The illustration in the drawings is schematic.

Referring now in greater detail to the drawings, FIG. 1 illustrates a sealing element according to embodiments of the herein disclosed subject matter.

The sealing element 100 is a structural element and is adapted for sealing a fluidic connection between a coupling element and a tubular element (not shown in FIG. 1). The sealing element 100 comprises a recess 102 extending in a longitudinal direction 104. The recess 102 is adapted for receiving a tubular element (not shown in FIG. 1). Further, the sealing element comprises a transverse wall defining an extent of the recess 102 in the longitudinal direction 104. The transverse wall 106 has a through hole 108.

The sealing element 100 comprises, in accordance with an embodiment, three retaining elements 110, two of which are shown in FIG. 1. The retaining elements are adapted for retaining a tubular element in the recess 102. According to an embodiment, the retaining elements 110 are adapted for clamping the tubular element. In this regard, it should be understood that according to an embodiment one type of sealing element 110 usually is adapted to a particular type of tubular element, i.e. the sealing element 110 is adapted to the dimensions and geometry of the tubular element in order to provide the function as disclosed herein with regard to embodiments of the herein disclosed subject matter. A type of tubular element may include for example two or more tubular elements having the same or similar outer diameter.

In accordance with an embodiment, the retaining elements 110 are protrusions that are located in the recess.

According to an embodiment, the sealing element comprises a conical outer surface portion 112 having a diameter increasing in a direction from the transverse wall 106 towards the recess 102. In accordance with an embodiment, the direction from the transverse wall 106 towards the recess 102 corresponds to the longitudinal direction 104 as shown in FIG. 1. Further, the direction from the transverse wall 106 towards the recess 102 may also be considered as a direction facing away from the transverse wall 106 or, a direction pointing from the recess outwardly through an opening (not shown in FIG. 1) through which a tubular element can be inserted into the recess 102.

In accordance with an embodiment, the sealing element comprises an inner surface portion 114 defining the recess, wherein the inner surface portion is opposite the conical outer surface portion 112. In accordance with an embodiment, the inner surface portion 114 and the conical outer surface portion 112 diverge from each other in the direction 104 from the transverse wall towards the recess 102, as shown in FIG. 1. According to a further embodiment, the inner surface portion 114 and the conical outer surface portion 112 are formed by a first longitudinal wall portion 116 extending over a longitudinal range 118. According to an embodiment, the first longitudinal wall portion 116 has a radial thickness 120 that increases in the longitudinal direction 104 from the transverse wall 106 towards the recess 102, as shown in FIG. 1. In accordance with an embodiment, the sealing element 100 comprises a cylindrical outer surface portion 122 having a constant diameter in the longitudinal direction 104. In accordance with an embodiment, the cylindrical outer surface portion is the outer surface of a second longitudinal wall portion 124 extending over a second longitudinal range 126. In accordance with an embodiment, the second longitudinal wall portion 122 is located between the transverse wall 106 and the conical outer surface portion 112. In accordance with a further embodiment, the second longitudinal wall portion 124 may be considered as being located between the transverse wall 106 and the first longitudinal wall portion 116. In accordance with an embodiment, the second longitudinal wall portion 124 has a radial wall thickness 128 that is constant in the direction 104 from the transverse wall 106 towards the recess 102.

The transverse wall 106 has a thickness 130 that may be adapted e.g. to the manufacturing process of the sealing element 100 and/or to the properties the transverse wall 106 must have in order to provide the functionality according to one or more of the embodiments of the herein disclosed subject matter. For example, according to an embodiment the thickness 130 of the transverse wall 106 is in a range between 0.05 millimeter to 0.1 millimeter.

According to an embodiment, the thickness 130 of the transverse wall 106 is about the same as the thickness 128 of the second longitudinal wall portion 124.

In accordance with an embodiment, the sealing element 100 comprises a polymer such as polyetheretherketone or consists of polyetheretherketone. Polyetheretherketone (PEEK) has the advantage that it is resistant against most of the liquids used in liquid chromatography and also it was found that PEEK has physical properties that are suitable to implement embodiments of the herein disclosed subject matter.

In accordance with an embodiment, the sealing element 100 is a single piece produced by injection molding. However, it should be understood that other production processes may also be suitable by providing the sealing element. Moreover, although the sealing element 100 shown in FIG. 1 is a single piece produced in a single injection molding step, in alternative embodiments, the sealing element consists of two or more parts which are attached to each other to form the sealing element providing the functionality as disclosed with regard to embodiments of the herein disclosed subject matter.

Figure 2:
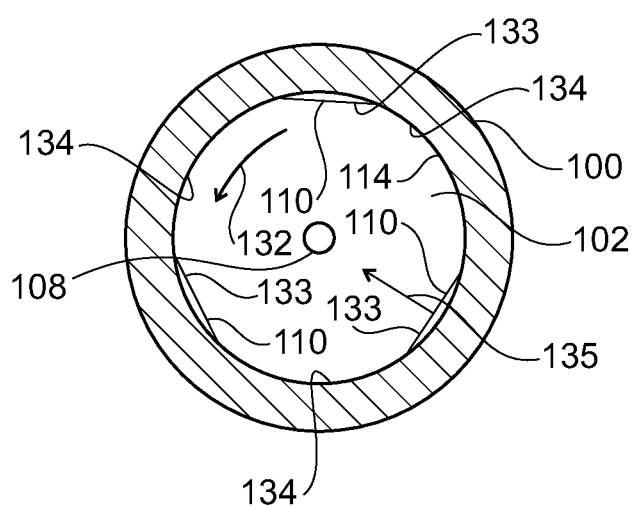
FIG. 2 shows a cross-sectional view of the sealing element of FIG. 1 along line II-II in FIG. 1.

FIG. 2 shows a cross-sectional view of the sealing element 100 of FIG. 1 along line II-II in FIG. 1.

In accordance with an embodiment, the sealing element 100 includes three retaining elements 110, the retaining elements 110 being spaced from each other in a circumferential direction 132. According to an embodiment, the circumferential direction 132 is a direction perpendicular to the longitudinal direction 104 along the inner surface portion 114 of the recess 102.

In accordance with an embodiment, the retaining elements 110 are formed in the recess 102 by a straight wall portion 133 extending between two curved wall portions 134 flanking the straight wall portion 133 in circumferential direction 132. In accordance with an embodiment, each of the retaining elements 110 exerts a radially inwardly directed force 135 on the tubular element (not shown in FIG. 2).

Figure 3:
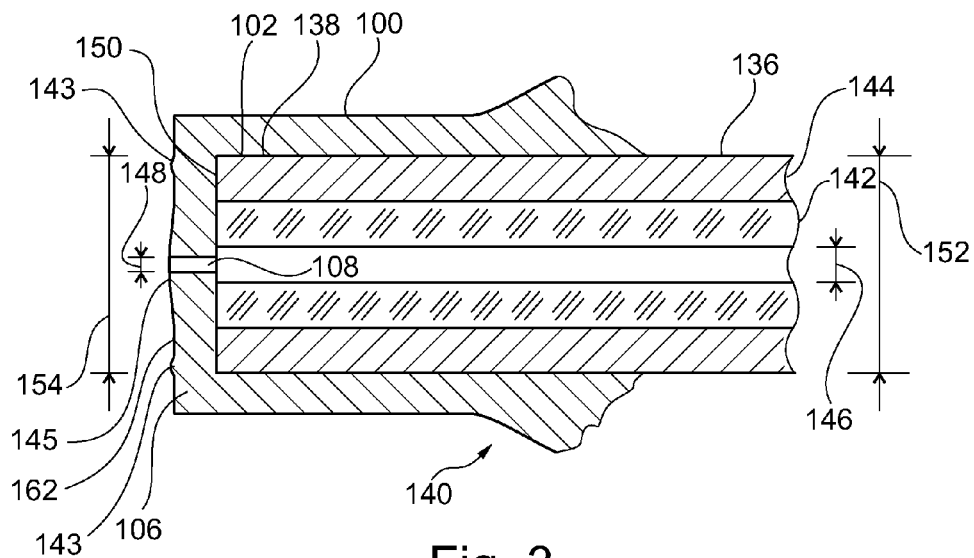
FIG. 3 shows the sealing element of according to embodiments of the herein disclosed subject matter with a tubular element inserted into the recess of the sealing element.

FIG. 3 shows the sealing element 100 according to embodiments of the herein disclosed subject matter with a tubular element 136 inserted into the recess 102 of the sealing element 100. Like elements are referred to with the same reference signs and the description thereof is not repeated here.

The retaining elements 110 (not shown in FIG. 3) retain the tubular element 136 in the recess 102. In particular, the retaining elements 110 exert a radially inwardly directed force on an outer surface 138 of the tubular element 136. The radially inwardly directed force is indicated at 135 in FIG. 2 and is not shown in FIG. 3 for the sake of clarity. Since each of the retaining elements 110 exerts a radially inwardly directed force 135 on the tubular element 136, the tubular element 136 in one embodiment being centered with regard to the recess 102. Further, the radially inwardly directed force 135 leads to a frictional force acting on the outer surface 138 of the tubular element 136, thereby preventing the sealing element 100 from slipping off the tubular element 136.

According to an embodiment, establishing a fluidic connection between a coupling element and the tubular element 136 includes inserting the tubular element 136 into the sealing element 100, thereby providing the tubular element 136 with the sealing element 100 mounted thereon. This preassembled mounting unit 140 may then be inserted or otherwise coupled to a coupling element (not shown in FIG. 3).

According to an embodiment, the tubular element 136 comprises a body 142 and a layer 144 covering the body 142. According to an embodiment, the body 142 is a capillary made of fused silica. According to a further embodiment, the layer 144 is a polymer layer such as a PEEK layer which protects the fused silica 142 from breakage during handling by a user. According to an embodiment, the tubular element 136 is a capillary as is commonly used in liquid chromatography applications, such as HPLC applications.

According to an embodiment, the inner diameter 146 of the tubular element 136 is larger than a diameter 148 of the through hole 108 in the transverse wall 106. This may have the advantage that the sealing between a front face 150 of the tubular element 136 and the coupling element (not shown in FIG. 3) can be improved. Moreover, according to an embodiment tolerances in the outer diameter 152 of the tubular element 136 or tolerances of the diameter of 154 of the recess 102 do not result in uncovered portions of the body 142 which are not covered by the transverse wall 106 of the sealing element 100. According to an embodiment the inner diameter 146 of the tubular element 136 is in a range between 100 micrometer and 500 micrometer whereas the diameter of 148 of the through hole 108 of the transverse wall 106 is in a range between 50 micrometer and 200 micrometer. For example, in an exemplary embodiment the inner diameter 146 of the tubular element 136 is 300 micrometer and the diameter 148 of the through hole 108 of the transverse wall 106 is 160 micrometer. According to a further embodiment, the outer diameter 152 of the tubular element 136 is 820 micrometer. In accordance with an embodiment, the tubular element 136 comprises a further layer covering the body 142 and the protective layer 144, i.e. the further layer and the protective layer 144 may be considered as sub-layers of the layer which covers the body 142. For example, in an embodiment such a further layer may be a polyamide layer.

According to an embodiment, the tubular element has a first hardness and a sealing element 100 has a second hardness smaller than the first hardness. In case the tubular element comprises two or more individual components such as the body 142 and the protective layer 144, the hardness of the tubular element is defined as to be the hardness of the hardest component of the tubular element. For example, according to an exemplary embodiment shown in FIG. 3, the hardness of the tubular element 136 is by definition the hardness of its hardest component, e.g. the hardness of the body 142. In accordance with an embodiment, the transverse wall 106 of the sealing element 100 undergoes plastic deformation if the tubular element 136, the sealing element 100 and the coupling element (not shown in FIG. 3) are brought into a connected state in which a sealed flow path through the tubular element, the coupling element and the through hole 108 in the transverse wall 106 of the sealing element is provided.

According to an embodiment, the transverse wall 106 of the sealing element has a protrusion structure 143 on its front face 162 which extends around the through hole 108 and is circumferentially closed so as to encircle the through hole 108. This may improve tightness of the sealing element 100 in the vicinity of the through hole 108. According to a further embodiment, the wall thickness of the transverse wall 106 in the vicinity of the through hole 108 is decreasing in a radially outward direction. In other words, in an embodiment the through hole 108 is formed in a central protrusion 145. According to an embodiment, the protrusion structure 143 is radially spaced from the central protrusion 145, as shown in FIG. 3.

Figure 4:
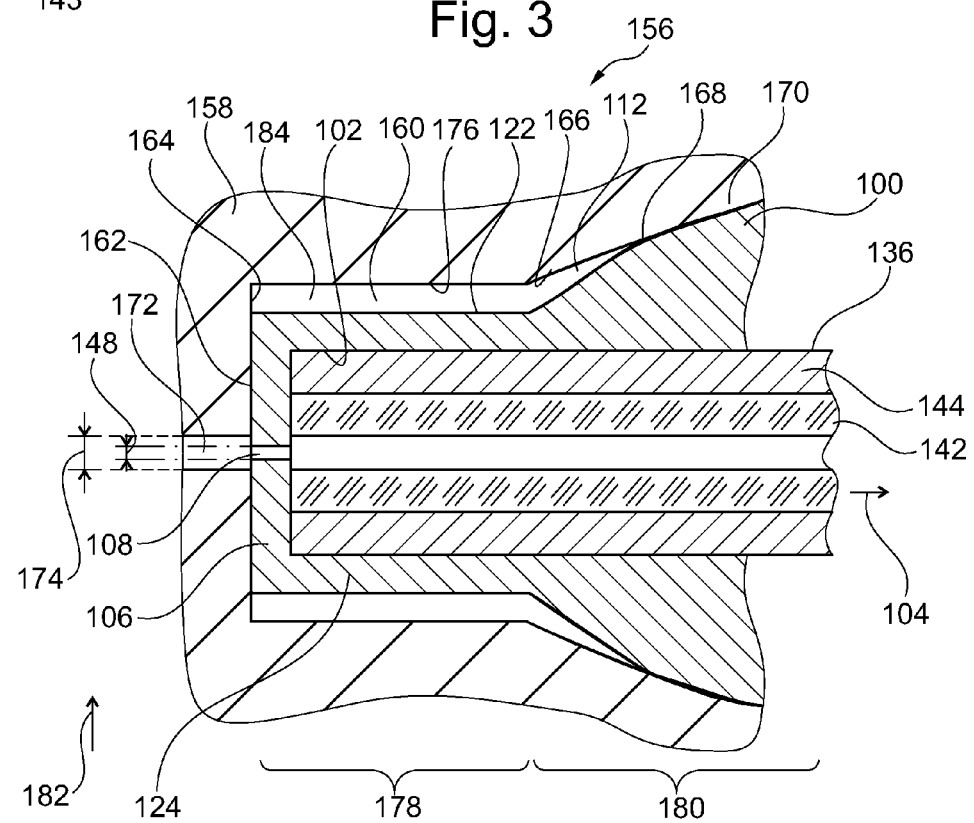
FIG. 4 shows a connection assembly according to embodiments of the herein disclosed subject matter.

FIG. 4 shows a connection assembly 156 according to embodiments of the herein disclosed subject matter.

According to an embodiment, the connection assembly 156 includes a coupling element 158, a tubular element 136 such as the tubular element 136 shown in FIG. 3 and comprising a body 142 and a protective layer 144. Further, in accordance with an embodiment the connection assembly 156 comprises a sealing element 100 in accordance with one or more embodiments of the herein disclosed subject matter. For example, in an exemplary embodiment the sealing element 100 is the sealing element 100 as shown in FIG. 1 to FIG. 3. Hence, the detailed description of the sealing element 100 is not repeated here.

In accordance with an embodiment, the connection assembly 156 provides a connected state in which the tubular element 136 is fluidically connected to the coupling element 158. This connected state is shown in FIG. 4.

In accordance with an embodiment, the coupling element 158 has a recess 160 for receiving the sealing element 100. According to a further embodiment, the recess 102 of the sealing element 100 is coaxially arranged with the recess 160 of the coupling element 158 in the connected state. In accordance with an embodiment, opposing faces of the sealing element 100 and the coupling element 158 provide for a well defined orientation (e.g. coaxial arrangement) of the sealing element 100 and the recess 160 of the coupling element 158. The opposing faces may e.g. be flat or, in another embodiment, curved. For example, a coaxial arrangement between the recess 102 of the sealing element 100 and the recess 160 of the coupling element may be achieved for example by a planar front face 162 of the transverse wall 106 of the sealing element 100 interacting with a planar bottom face 164 of the recess 160 of the coupling element 158. In accordance with an embodiment, the planar faces 164, 162 provide for a well defined orientation of the sealing element 100 and the recess 160 of the coupling element 158. However, the front face 162 of the sealing element 100 is not necessarily planar or flat. It can be structured as well. For example it can provide circular type elevated structures or a serrated-concentric finish. According to an embodiment the opposing faces, e.g. the opposing faces 162, 164, provide for a parallel alignment of the recess 102 of the sealing element and the recess 160 of the coupling element 158. In addition to that, the conical outer surface portions 112 of the sealing element 100 together with opposing conical inner surface portions 166 of the recess 160 of the coupling element 158 provide for the coaxial alignment of the recess 102 of the sealing element 100 and the recess 160 of the coupling element 158.

According to an embodiment, the recess 160 of the coupling element 158 comprises a conical inner surface portion having a diameter which increases in a direction pointing outwardly from the recess 160 of the coupling element 158 through an opening (not shown in FIG. 4) which is defined by the recess 160 and through which the sealing element 100 is inserted into the recess 160 of the coupling element 158. In accordance with an embodiment, this conical inner surface portion is identical to the conical inner surface portion 166 described before.

In the following, it is referred to only the conical inner surface portion 166. However, unless otherwise notified, reference to the conical inner surface portion 166 shall be only a reference to a conical inner surface portion having a diameter which increases in a direction pointing outwardly from the recess 160 of the coupling element 158 through an opening which is defined by the recess 160 of the coupling element and through which the sealing element 100 is inserted into the recess 160 of the coupling element 158.

According to an embodiment, in the connected state the conical inner surface portion 166 of the coupling element 158 and the conical outer surface portion 112 of the sealing element 100 at least partially overlap in the longitudinal direction 104. In accordance with an embodiment, the conical inner surface portion 166 of the coupling element 158 has a first slope and the conical outer surface of the sealing element has a second slope wherein the first slope and the second slope are different. Further, according to an embodiment the second slope of the conical outer surface portion 112 of the sealing element is steeper with regard to the longitudinal direction 104 than the first slope of the conical inner surface portion 166 of the coupling element, as shown in FIG. 4. This leads to a configuration where a contact line which is a boundary of a contact area between the conical inner surface portion 166 of the coupling element 158 and the conical outer surface portion 112 of the sealing element 100 moves in a direction into the recess 160 of the coupling element if the sealing element is pushed further into the recess 160. According to an embodiment, the coupling element 158 and the sealing element 100 are configured such that without longitudinal pressure on the sealing element into the recess 160 of the coupling element only a contact portion 170 of the conical outer surface 112 of the sealing element contacts the conical inner surface 166 of the coupling element 158, wherein the contact portion 170 has a smaller area than the conical outer surface portion 112 of the sealing element.

According to an embodiment, the coupling element 158 comprises a through hole 172, wherein in the connected stage shown in FIG. 4 the through hole of 172 of the coupling element 158 is fluidically coupled to the through hole 108 of the transverse wall 106 of the sealing element 100. According to an embodiment, the diameter 174 of the through hole 172 of the coupling element 158 is larger than the diameter 148 of the through hole 108 of the transverse wall 106 of the sealing element. According to an embodiment, this provides for a save sealing of the fluidic connection between the coupling element 158 and the tubular element 136 even if the sealing element 100 is not perfectly aligned with the through hole 172 of the coupling element 158. Further according to an embodiment, the diameter 174 of the through hole 172 of the coupling element 158 is larger than the inner diameter 146 of the tubular element 136 (see FIG. 3). However, according to other embodiments the diameter 174 of the through hole 172 is equal to or smaller than the inner diameter 146 of the tubular element 136.

According to a further embodiment, the recess 160 of the coupling element 158 comprises a cylindrical inner surface portion 176, wherein in the connected state the cylindrical inner surface portion of the coupling element 158 and the cylindrical outer surface portion 122 of the sealing element 100 at least partially overlap in longitudinal direction 104. According to an embodiment, the cylindrical inner surface portion 176 extends over a longitudinal range 178 and the conical inner surface portion 166 of the coupling element 158 extends over a longitudinal range 180. According to an embodiment, the longitudinal range 126 over which the cylindrical wall portion 124 of the sealing element 100 extends plus the thickness 130 of the transverse wall 106 is equal to or larger than the extend of the longitudinal range 178 of the cylindrical inner surface portion 176 of the coupling element 158. In such a case, the longitudinal wall portion 124 of the sealing element is compressed in the longitudinal direction 104 before the conical outer surface portion 112 of the sealing element 100 is fully engaged with the conical inner surface portion 166 of the coupling element. This compression on the one hand pushes the transverse wall 106 with a defined force against the bottom 164 of the recess 160 of the coupling element 158. Further, depending on the material properties of the material of the sealing element 100 and the degree of compression, the cylindrical wall portion 124 of the sealing element 100 may extend in radial direction 182, thereby reducing a space 184 between the cylindrical inner surface portion 176 of the coupling element 158 and the cylindrical outer surface portion 122 of the sealing element 100.

Figure 5:
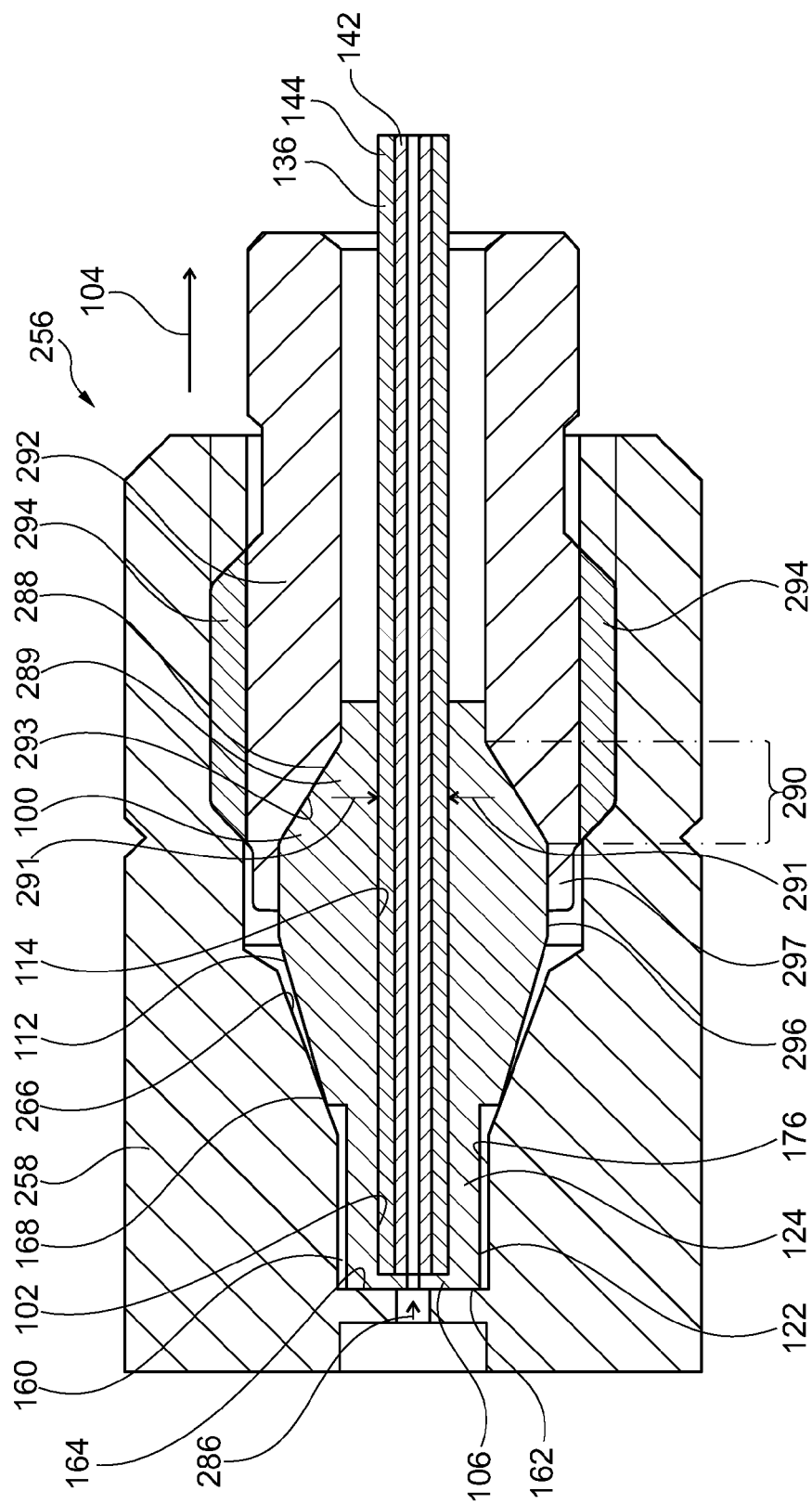
FIG. 5 shows a further connection assembly according to embodiments of the herein disclosed subject matter.

FIG. 5 shows a further connection assembly 256 according to embodiments of the herein disclosed subject matter. The connection assembly 256 comprises features similar to the features described with regard to FIG. 1 to 4 and the detailed description thereof is not repeated here. Rather with regard to FIG. 5 differences or additional features of the connection assembly 256 are described.

In accordance with an embodiment, of the connection assembly 256 a first slope of the conical inner surface portion 266 of a coupling element 258 is steeper with regard to the longitudinal direction 104 than a second slope of the conical outer surface 112 of the sealing element 100. According to an embodiment an longitudinally inner contact line 168 is formed as a boundary of the contact area between the conical inner surface portion 266 of the coupling element 258 and the conical outer surface portion 112 of the sealing element 100, wherein the longitudinally inner contact line 168 faces the faces the bottom 164 of the recess 160 of the coupling element 258. The slopes of the conical inner surface portion 266 of the coupling element 258 and the conical outer surface portion 112 of the sealing element 100, which diverge in the direction 104 from the transverse wall 106 towards the recess 102 of the sealing element 100, have the advantage that if the sealing element 100 is pushed in direction 104, e.g. under high pressure of a liquid in a flow path 286, the longitudinally inner contact line 168 does not move or moves only to very low extent. Hence even under varying pressure in the flow path 286 the connection assembly 256 does not breathe or does breathe only to a small extent. Accordingly, even if there is a gap between the sealing element 100 and the recess 160 of the coupling element 258, and even if this gap is filled with fluid during initial pressurizing the flow path 286, the fluid in the gap is harmless under certain pressure variations, e.g. pressure variations that occur during a measurement run of a chromatography application since under these pressure variations the gap does not change volume (i.e. it does not breathe) or it changes volume only to a negligible extent.

According to an embodiment, the sealing element 100 comprises a compression surface 288 being spaced from the transverse wall 106. According to an embodiment, the compression surface 288 is the outer surface of a third longitudinal wall portion 289 of the sealing element 100. The third longitudinal wall portion 289 extends over a longitudinal range 290. In accordance with an embodiment, the compression surface 288 has a conical shape with a diameter decreasing in the direction 104 from the transverse wall 106 towards the recess 102 of the sealing element 100. According to an embodiment, the third longitudinal wall portion 289 comprises a cutout (not shown in FIG. 5) which extends in longitudinal direction 104 wherein the cutout forms a longitudinal slit. In conjunction with the conical shape of the compression surface this results in a forced transfer from the conical compression surface 288 to the inner surface 114 of the sealing element, thereby resulting in radially inwardly directed force on the tubular element 136. The radially inwardly directed force onto the tubular element 136 is indicated at 291 in FIG. 5. The radially inwardly directed force 291 of the sealing element 100 onto the tubular element 136 provides a frictional force by which a further inward movement of the sealing element 100 by action of a further inward movement of the compression surface 288 pushes the tubular element 136 towards the transverse wall 106 of the sealing element.

In accordance with an embodiment, the connection assembly 256 comprises a pressing element 292 for pressing against the compression surface 288. The pressing element 292 comprises a pressing surface 293 and is configured for pressing the sealing element 100 into the recess 160 of the coupling element 258. According to an embodiment, the compression of the sealing element 100 by movement of the pressing element 292 leads to a contact of the transverse wall of the sealing element and the bottom 164 of the recess 160 of the coupling element 258. Upon further movement of the pressing element towards the bottom 164 of the recess 160 of the coupling element 258, the conical outer surface portion 112 of the sealing element 100 gets in contact with the conical inner surface portion 266 of the coupling element 258. Further, the second longitudinal wall portion 124 is compressed in longitudinal direction 104. As discussed before, this may lead to an extension of the second longitudinal wall portion 124 in radial direction, thereby reducing a space between the cylindrical outer surface portion 122 of the sealing element and the cylindrical inner surface portion 176 of the coupling element.

According to an embodiment, the pressing element 292 comprises a thread engagable with a thread of a coupling element 258 so that the pressing element 292 is movable in longitudinal direction 104 by rotating the pressing element 292. The threaded engagement of the pressing element 292 and the coupling element 258 is indicated at 294 in FIG. 5.

Having regard to the assembly process of the connection assembly 256, according to an embodiment first the tubular element 136 is inserted into the recess 102 of the sealing element 100, preferably until the tubular element 136 contacts the transverse wall 106 of the sealing element. In accordance with an embodiment, in this position the sealing element 100 is retained on the tubular element 136 by the retaining elements (not shown in FIG. 5) provided in the recess 102.

Next, this preassembled mounting unit comprising the tubular element 136 and the sealing element 100 is inserted into the recess 160 of the coupling element 258. Depending on the actual embodiment, already during this initial insertion the front face 162 of the transverse wall portion 106 of the sealing element 100 may contact the bottom 164 of the recess 160 which faces the transverse wall 106 of the sealing element. According to other embodiments, the longitudinal range 126 and the configuration of the conical outer surface portion 112 of the sealing element may be such that at first the conical outer surface portion 112 of the sealing element contacts the conical inner surface portion 266 of the coupling element 258. However, according to a preferred embodiment, the front face 162 of the transverse wall 106 first contacts the bottom 164 of the coupling element 258 before the conical surface portions 266, 112 contact each other. According to a further embodiment the contact between transverse wall 106 and bottom 164 occurs simultaneously with the contacting of the conical surfaces 112, 266. However, upon further movement of the compression surface 288 of the sealing element 100 towards the bottom 164 which faces the transverse wall 106 of the sealing element 100 results in an increasing contact area between the conical surfaces 266, 112 of the coupling element 258 and the sealing element 100, to a frictional engagement of the tubular element 136 by the sealing element 100 and therefore, upon further movement of the compression surface 288 towards the bottom 164, to a compression of the transverse wall 106 between the tubular element 136 and the bottom 164. According to an embodiment, the frictional engagement between the sealing element and the tubular element and hence movement of the tubular element 136 against the transverse wall 106 occurs only after the transverse wall 106 has contacted the bottom 164, e.g. by respective configuration of the sealing element 100, the tubular element 136, and the coupling element 258. This prevents a breakage of the transverse wall 106 upon tightening the connection assembly 256.

According to an embodiment, the sealing element 100 comprises a fourth outer surface portion 296 which is for example a cylindrical outer surface portion. The fourth outer surface portion 296 of the sealing element is located between the compression surface 288 and the conical outer surface portion 112 of the sealing element. According to an embodiment, the pressing element 292 comprises an annular protrusion 297 which extends at least partially over the fourth outer surface portion 296 of the sealing element, e.g. to thereby prevent deformation of the fourth outer surface portion 296 under the compressive force exerted by the pressing surface 293 onto the sealing element. The annular protrusion 297 may provide an improved force transfer in longitudinal direction from the pressing element 292 to the transverse wall 106.

Figure 6:
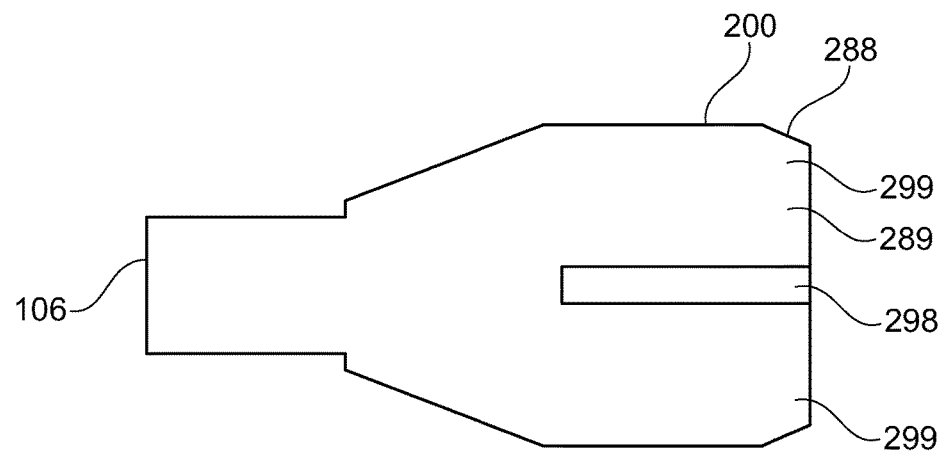
FIG. 6 shows a sealing element in accordance with embodiments of the herein disclosed subject matter.

FIG. 6 shows a sealing element 200 in accordance with embodiments of the herein disclosed subject matter.

The sealing element 200 comprises features as described with regard to FIG. 1 to 5 above, the detailed description of which is not repeated here. Rather with regard to FIG. 6 additional features are described.

In accordance with an embodiment, the compression surface 288 forms a second end of the sealing element 200, the second end being opposite the first end which is formed by the transverse wall 106. In accordance with a further embodiment, the third longitudinal wall portion 289 which forms the compression surface 288 comprises a cutout 298 in the form of a slit which reduces a radial force onto respective opposing portions 299 of the third longitudinal wall portion 289 of the sealing element that is necessary to move the opposing portions 299 towards each other to reduce the width of the slit 298. Moving the opposing portions 299 towards each other leads to frictional engagement of the opposing portions 299 and the tubular element 136 (not shown in FIG. 6).

Figure 7:
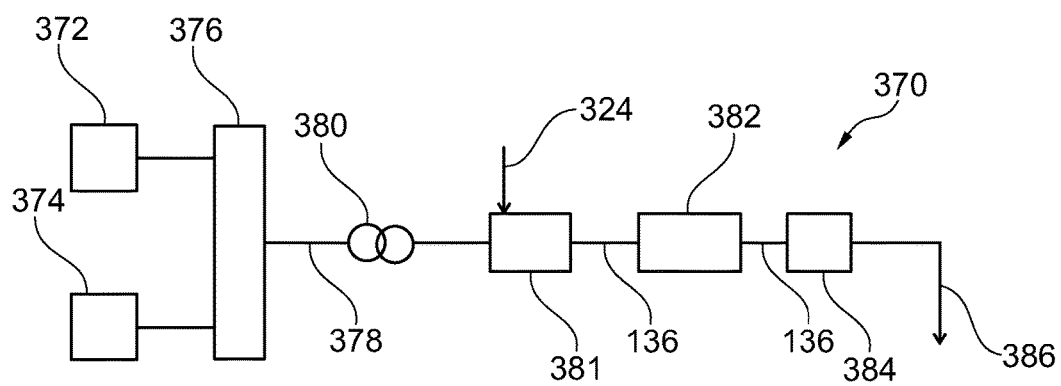
FIG. 7 shows a measuring device in accordance with embodiments of the herein disclosed subject-matter.

FIG. 7 shows a measuring device 370 in accordance with embodiments of the herein disclosed subject-matter.

In accordance with an embodiment, the measuring device 370 comprises two reservoirs 372, 374 which are fluidically coupled to a proportioning valve 376, wherein the proportioning valve 376 provides a mobile phase 378 containing at least one of the liquids of the two reservoirs 372, 374 to a fluid drive unit 380. In accordance with an embodiment, the measuring device 370 comprises the fluid drive unit 380, such as a pump, in order to drive the mobile phase 378 through an injection device 381, where a pressurized sample fluid 324 is injected into the mobile phase 378.

In accordance with an embodiment, the measuring device 370 comprises a separation unit 382, such as a chromatographic column. In accordance with an embodiment, the separation unit 382 is configured for separating compounds of the sample fluid in the mobile phase 378. Further in accordance with an embodiment, the measuring device 370 comprises a detector 384 for detecting the separated compounds of the sample fluid 324 in the mobile phase. Downstream the detector 384, the mobile phase 378 and the sample fluid 324 may be provided to a waste, indicated at 386 in FIG. 7. A connection assembly implementing one or more embodiments of the herein disclosed subject matter may be used for sealing any fluidic connection in the measuring device 370. For example, such a connection assembly may be used for connecting the injection device 381, a separation unit 382 and/or the detector 384 with a respective tubular element 136 in the form of a capillary, just to name some examples. It should be understood that according to an embodiment the coupling element according to one or more embodiments of the herein disclosed subject matter is a part of a component of the measuring device, e.g. a part of the injection device 381, of the separation unit 382 and/or of the detector 384.

It should be noted that any entity disclosed herein, (e.g. a component, element, unit, device) is not limited to a dedicated entity as described in some embodiments. Rather, the herein disclosed subject-matter may be implemented in various ways and with various granularity on device level while still providing the desired functionality. Further, it should be noted that according to embodiments a separate entity (e.g. a component, element, unit, device) may be provided for each of the functions disclosed herein. According to other embodiments, an entity is configured for providing two or more functions as disclosed herein.

It should be noted that any embodiment disclosed herein may be combined with one or more other embodiments disclosed herein unless otherwise noted or unless technically infeasible.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A sealing element for sealing a fluidic connection between a coupling element and a tubular element and thereby providing a sealed flow path through the tubular element and between the coupling element and the tubular element in a longitudinal direction, the sealing element comprising:
a single piece tapered unit comprising:
a recess extending in the longitudinal direction, the recess configured to receive the tubular element; and
a transverse wall defining an extent of the recess in the longitudinal direction and upon which a front end of the tubular element seals when disposed in the recess, the transverse wall having a through hole.

2. The sealing element of claim 1, wherein:
the recess comprises at least one retaining element for retaining the tubular element in the recess; and
the sealing element further comprising a feature selected from the group consisting of:
the sealing element includes at least three of the retaining elements, the at least three retaining elements being spaced from each other in a circumferential direction;
the at least one retaining element is configured to exert a radially inwardly directed force onto the tubular element;
the at least one retaining element is a protrusion located in the recess;
the at least one retaining element is formed in the recess by a straight wall portion extending between two curved wall portions flanking the straight wall portion in circumferential directions; and
the at least one retaining element extends radially inwardly to clamp and center the tubular element.

3. The sealing element of claim 1, further comprising:
a conical outer surface portion, the conical outer surface portion having a diameter increasing in a direction from the transverse wall towards an opening of the recess, thereby forming a taper of the single piece tapered unit;
wherein the sealing element comprises an inner surface portion defining the recess, wherein the inner surface portion is opposite the conical outer surface portion, and
wherein the sealing element further comprises a feature selected from the group consisting of:
the inner surface portion and the conical outer surface portion diverge from each other in the direction from the transverse wall towards the recess; and
the inner surface portion and the conical outer surface portion are formed by a first longitudinal wall portion with a radial thickness that increases in the direction from the transverse wall towards the recess.

4. The sealing element of claim 1, further comprising:
a cylindrical outer surface portion having a constant diameter in the longitudinal direction;
wherein the sealing element comprises a feature selected from the group consisting of:
the cylindrical outer surface portion is the outer surface of a second longitudinal wall portion,
the second longitudinal wall portion is located between the transverse wall and the first longitudinal wall portion; and
the second longitudinal wall portion has a radial wall thickness that is constant in the direction from the transverse wall towards the recess.

5. The sealing element of claim 1, further comprising:
a compression surface being spaced from the transverse wall, the compression surface comprising a feature selected from the group consisting of:
the compression surface is the outer surface of a third longitudinal wall portion of the sealing element;
the third longitudinal wall portion comprises a cutout extending in the longitudinal direction, wherein the cutout is a longitudinal slit, wherein the longitudinal slit has a sharp-edged end in a direction to the sealing face, or wherein the longitudinal slit has one of a rectangular end and a rounded end;
the third longitudinal wall portion comprises three or more cutouts and wherein the three or more cutouts are evenly spread or nonuniformly distributed over the circumference;

the compression surface has a conical shape with a diameter decreasing in a direction from the transverse wall towards the recess of the sealing element; and the transverse wall forms a first end of the sealing element and the compression surface forms second end of the sealing element, the second end being opposite the first end.

6. The sealing element of claim 1, wherein the sealing element comprises one selected from the group consisting of a polymer, a polyether, and a polyetheretherketone.

7. The sealing element of claim 1, further comprising a feature selected from the group consisting of:
the sealing element is a molded single piece; and
the sealing element is injection molded as a single piece.

8. A connection assembly, comprising:
a coupling element;
a tubular element fluidically connectable or fluidically connected to the coupling element; and
a sealing element comprising:
a single piece tapered unit comprising:
a recess extending in the longitudinal direction, the recess configured to receive the tubular element; and
a transverse wall defining an extent of the recess in the longitudinal direction and upon which a front end of the tubular element seals when disposed in the recess, the transverse wall having a through hole,
wherein the connection assembly provides a connected state in which the tubular element is fluidically connected to the coupling element.

9. The connection assembly of claim 8, further comprising:
the coupling element having a recess configured to receive the sealing element;
wherein the connection assembly comprises a feature selected from the group consisting of:
in the connected state the recess of the coupling element is arranged coaxially with the recess of the sealing element;
the coupling element comprises a through hole wherein in the connected state the through hole of the coupling element is fluidically coupled to the through hole of the transverse wall of the sealing element;
the diameter of the through hole of the coupling element is larger than the diameter of the through hole of the transverse wall of the sealing element; and
the diameter of the through hole in the transverse wall of the sealing element is smaller than the inner diameter of the tubular element.

10. The connection assembly of claim 8,
wherein the sealing element comprises a conical outer surface portion, the conical outer surface portion having a diameter increasing in a direction from the transverse wall towards an opening of the recess, thereby forming a taper of the single piece tapered unit;
wherein the sealing element comprises an inner surface portion defining the recess, wherein the inner surface portion is opposite the conical outer surface portion and wherein the sealing element further comprises a feature selected from the group consisting of:
wherein the inner surface portion and the conical outer surface portion diverge from each other in the direction from the transverse wall towards the recess,
wherein the inner surface portion and the conical outer surface portion are formed by a first longitudinal wall portion with a radial thickness that increases in the direction from the transverse wall towards the recess;
wherein the recess of the coupling element comprises a conical inner surface portion having a diameter which increases in a direction pointing outwardly from recess of the coupling element through an opening which is defined by the recess and through which the sealing element is inserted; and
wherein in the connected state the conical inner surface portion of the coupling element and the conical outer surface portion of the sealing element at least partially overlap in longitudinal direction;
wherein the connection assembly further comprises a feature selected from the group consisting of:
wherein the conical inner surface portion of the coupling element has a first slope and the conical outer surface portion of the sealing element has a second slope, wherein the first slope and the second slope are different;
wherein the first slope is steeper with regard to the longitudinal direction than the second slope; and
wherein the coupling element and the sealing element are configured such that without longitudinal pressure on the sealing element only a contact portion of the conical outer surface portion of the sealing element contacts the conical inner surface portion of the coupling element, wherein the contact portion has a smaller area than the conical outer surface portion; and wherein the coupling element and the sealing element are configured such that a contact line of the sealing element is facing the transverse wall of the sealing element.

11. The connection assembly of claim 8,
wherein the sealing element further comprises a cylindrical outer surface portion having a constant diameter in the longitudinal direction;
wherein the sealing element comprises a feature selected from the group consisting of:
a) wherein the cylindrical outer surface portion is the outer surface of a second longitudinal wall portion, the second longitudinal wall portion comprising a feature selected from the group consisting of:
wherein the second longitudinal wall portion is located between the transverse wall and the first longitudinal wall portion; and
wherein the second longitudinal wall portion has a radial wall thickness that is constant in the direction from the transverse wall towards the recess; and the recess of the coupling element comprises a cylindrical inner surface portion, wherein in the connected state the cylindrical inner surface portion of the coupling element and the cylindrical outer surface portion of the sealing element at least partially overlap in longitudinal direction; and
b) wherein the sealing element is configured such that in the connected state the second longitudinal wall portion, which forms the cylindrical outer surface portion of the sealing element, is compressed in longitudinal direction so as to expand in radial direction and thereby reduce a space between the cylindrical inner surface portion of the coupling element and the cylindrical outer surface portion of the sealing element.

12. The connection assembly of claim 8,
wherein the sealing element comprises a compression surface being spaced from the transverse wall, the compression surface comprising a feature selected from the group consisting of:
the compression surface is the outer surface of a third longitudinal wall portion of the sealing element;
the third longitudinal wall portion comprises a cutout extending in the longitudinal direction wherein the cutout is a longitudinal slit, wherein the longitudinal slit has a sharp-edged end in a direction to the sealing face,
or wherein the longitudinal slit has one of a rectangular end and a rounded end;
the third longitudinal wall portion comprises three or more cutouts and wherein the three or more cutouts are evenly spread or nonuniformly distributed over the circumference;
the compression surface has a conical shape with a diameter decreasing in a direction from the transverse wall towards the recess of the sealing element; and
the transverse wall forms a first end of the sealing element and the compression surface forms second end of the sealing element, the second end being opposite the first end; and
the connection assembly further comprising a pressing element for pressing against the compression surface, the pressing element comprising a feature selected from the group consisting of:
the pressing element has pressing surface, and
the pressing element is configured for pressing the sealing element into the recess of the coupling element;
wherein compression of the sealing element by movement of pressing element comprises a feature selected from the group consisting of:
the transverse wall of the sealing element contacts the recess of the coupling element;
the conical outer surface portion of the sealing element at least partially contacts the conical inner surface portion of the coupling element;
the second longitudinal wall portion of the sealing element is compressed in longitudinal direction; and
the sealing element radially presses against the tubular element located in the recess of the sealing element.

13. The connection assembly of claim 8, further comprising a feature selected from the group consisting of:
the tubular element has a first hardness and the sealing element has a second hardness smaller than the first hardness;
the tubular element comprises silicon dioxide;
the tubular element comprises a glass;
the tubular element comprises a body and a layer covering the body, wherein the layer is a protective layer;
the tubular element comprises fused silica;
the tubular element comprises steel;
the coupling element is a fitting;
the tubular element is a capillary; and
the sealing element is configured for providing a sealed fluidic connection between the coupling element and the tubular element, wherein the fluidic connection is configured to withstand a pressure of at least 1000 bar.

14. A measuring device for performing a measurement on a fluidic sample, the measuring device comprising:
a fluidic device;
a connection assembly for coupling the tubular element for conducting the fluidic sample to the fluidic device;
the connection assembly comprising:
a coupling element;
a tubular element fluidically connectable or fluidically connected to the coupling element; and
a sealing element comprising:
a recess extending in the longitudinal direction, the recess configured to receive the tubular element; and
a transverse wall defining an extent of the recess in the longitudinal direction, the transverse wall having a through hole,
wherein the connection assembly provides a connected state in which the tubular element is fluidically connected to the coupling element,
wherein the fluidic sample is a mobile phase and the measuring device is a fluid separation system for separating compounds of a sample fluid in the mobile phase,
the fluid separation system comprising:
a mobile phase drive, configured to drive the mobile phase through the fluid separation system,
wherein the fluidic device is a separation unit, configured to separate compounds of the sample fluid in the mobile phase.

15. A method for providing a fluidic connection between a coupling element and a tubular element, the method comprising:
a) providing a connection assembly comprising:
a coupling element;
a tubular element fluidically connectable or fluidically connected to the coupling element, and
a sealing element comprising:
a single piece tapered unit comprising:
a recess extending in the longitudinal direction, the recess being adapted for receiving the tubular element; and
a transverse wall defining an extent of the recess in the longitudinal direction and upon which a front end of the tubular element seals when disposed in the recess, the transverse wall having a through hole,
wherein the connection assembly provides a connected state in which the tubular element is fluidically connected to the coupling element;
b) inserting the tubular element into the sealing element; and
c) inserting the sealing element into the recess of the coupling element.

16. The method of claim 15,
wherein the sealing element comprises a compression surface being spaced from the transverse wall
the connection assembly further comprising a pressing element configured to press against the compression surface,
the method further comprising:
operating the pressing element so as to press the sealing element into the recess of the coupling element;
wherein the method further comprises a feature selected from the group consisting of:
pressing the transverse wall of the sealing element in contact with the recess of the coupling element;
pressing at least part of the conical outer surface portion of the sealing element into contact with the conical inner surface portion of the coupling element;
longitudinally compressing the sealing element so as to longitudinally compress the second longitudinal wall portion of the sealing element in the longitudinal direction;

compressing the sealing element so as to radially press the sealing element against the tubular element located in the recess of the sealing element;

frictionally engaging the tubular element by the sealing element and moving together the sealing element and the tubular element deeper into the recess so as to compress the transverse wall between the tubular element and a bottom of the recess of the coupling element opposite the transverse wall.

17. The method of claim 16, wherein the compression surface comprises a feature selected from the group consisting of:

the compression surface is the outer surface of a third longitudinal wall portion of the sealing element;

the third longitudinal wall portion comprises a cutout extending in the longitudinal direction wherein the cutout is a longitudinal slit wherein the longitudinal slit has a sharp-edged end in a direction to the sealing face or wherein the longitudinal slit has one of a rectangular end and a rounded end;

the third longitudinal wall portion comprises three or more cutouts and wherein the three or more cutouts are evenly spread or nonuniformly distributed over the circumference;

the compression surface has a conical shape with a diameter decreasing in a direction from the transverse wall towards the recess of the sealing element; and the transverse wall forms a first end of the sealing element and the compression surface forms second end of the sealing element, the second end being opposite the first end.

18. The method of claim 16, wherein the pressing element comprises a feature selected from the group consisting of:

the pressing element has pressing surface, and the pressing element is configured for pressing the sealing element into the recess of the coupling element.

19. The method of claim 16, wherein compression of the sealing element by movement of pressing element comprises a feature selected from the group consisting of:

the transverse wall of the sealing element contacts the recess of the coupling element;

the conical outer surface portion of the sealing element at least partially contacts the conical inner surface portion of the coupling element;

the second longitudinal wall portion of the sealing element is compressed in longitudinal direction; and the sealing element radially presses against the tubular element located in the recess of the sealing element.

20. The sealing element of claim 1, wherein a longitudinal wall portion of the tapered unit is compressed in the longitudinal direction before a conical outer surface portion of the tapered unit is fully engaged with a conical inner surface portion of the coupling element.

\* \* \* \* \*